US012085225B2

(12) United States Patent
Jones et al.

(10) Patent No.: US 12,085,225 B2
(45) Date of Patent: Sep. 10, 2024

(54) SURGICAL ROBOT SUPPORT WITH PATIENT POSITIONER

(71) Applicant: DePuy Ireland Unlimited Company, Ringaskiddy (IE)

(72) Inventors: Michael Jones, North Webster, IN (US); Robert John Wright, Dedham, MA (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 303 days.

(21) Appl. No.: 17/825,131

(22) Filed: May 26, 2022

(65) Prior Publication Data

US 2022/0381398 A1 Dec. 1, 2022

Related U.S. Application Data

(60) Provisional application No. 63/194,752, filed on May 28, 2021.

(51) Int. Cl.
   *A61B 90/50* (2016.01)
   *A61B 5/00* (2006.01)
   *F16M 13/02* (2006.01)

(52) U.S. Cl.
   CPC .............. *F16M 13/022* (2013.01); *A61B 5/70* (2013.01); *A61B 90/50* (2016.02)

(58) Field of Classification Search
   CPC .......... F16M 13/02; A61B 90/50; A61B 34/30

USPC ......................................... 248/674; 128/99.1
See application file for complete search history.

(56) References Cited

U.S. PATENT DOCUMENTS

| | | | |
|---|---|---|---|
| 10,357,416 B2 * | 7/2019 | Cole .................... | A61G 13/125 |
| 10,820,866 B2 * | 11/2020 | Campagna ........... | A61G 13/122 |
| 11,076,817 B2 * | 8/2021 | Campagna .............. | A61B 6/04 |
| 11,602,399 B2 * | 3/2023 | Urvoy ................ | A61G 13/1245 |
| 11,648,165 B2 * | 5/2023 | Mahoney ............... | A61G 13/12 5/624 |
| 11,786,188 B2 * | 10/2023 | Campagna ......... | A61G 13/1245 128/845 |
| 11,925,586 B2 * | 3/2024 | Lim ..................... | A61G 13/121 |

* cited by examiner

*Primary Examiner* — Todd M Epps
(74) *Attorney, Agent, or Firm* — Condo Roccia Koptiw LLP

(57) ABSTRACT

Systems, methods, and devices are disclosed for holding devices for securing a surgical robotic device and a patient anatomy positioner to a support (e.g., in an operating room). A holding device comprises a carriage, an anchor component fixed to the carriage for attaching to the support, a patient stabilization connector extending from the anchor component for attaching to the patient positioner, and an elongate holder slidably mounted on the carriage for attaching to the robotic device, wherein, when the anchor component is attached to the support, the carriage and the patient stabilization connector are immobilized. The holding devices may also include a hydraulic cylinder interposed between the elongate holder and carriage and/or a horizontal linkage interposed between the elongate holder and the robotic device.

20 Claims, 13 Drawing Sheets

SURGICAL ROBOT SUPPORT WITH PATIENT POSITIONER

CROSS-REFERENCE TO RELATED APPLICATION

This application claims priority to U.S. Provisional Ser. No. 63/194,752, filed May 28, 2021, the disclosure of which is incorporated herein in its entirety.

BACKGROUND

Surgical procedures may require support for at least a portion of a patient's anatomy. A patient stabilizer (hereinafter "positioner") may place, maintain, and/or immobilize the patient or a portion of patient anatomy in a desired position. For example, if a surgical plan calls for a certain flexed knee position, the positioner is secured to an operating table (such as a bed rail) or other operating room structure, and then engaged under or beside the patient's knee in accordance with the surgical plan. The positioner may comprise a pad for engaging the patient anatomy, an arm, and a connector (e.g., for engaging the operating room structure). At least a portion of the positioner may be covered with a drape.

In a robotic or robot-assisted surgical procedure, a surgical robot (e.g., a robotic arm), hereinafter referred to as a robotic device, may guide or control one or more surgical instruments, such as a saw, drill, etc. Further to the above knee procedure example, the robotic device may also be coupled to the operating table (e.g., the bed rail). Each may be separately attached to the operating table bed rail at distinct locations. However, as can be appreciated, both the patient positioner and the robotic device should be placed in close proximity to the patient anatomy to be operated on.

Moreover, placement of the robotic device may restrict or even block certain locations (e.g., along the bed rail) from being available for attachment by the patient positioner. For example, the robotic device may already occupy a location that may also be highly desirable for mounting one or more patient positioners (e.g., in order to position the patient anatomy in the vicinity of the robotic device). As a result, the patient positioner will have to be placed elsewhere, and thus contact between the patient positioner and the patient anatomy may occur at a sub-optimal location and/or may require significant maneuvering of the patient positioner once the robotic device is placed to achieve the desired stability of patient anatomy during the surgical procedure. Moreover, in its turn, the robotic device may have to discover the location of the patient positioner (e.g., or testing may need to be done) to confirm that the patient positioner will not interfere with operation of the robotic device pursuant to the surgical plan.

Accordingly, there is a need for improved systems, methods, and devices for positioning and stabilizing at least a portion of patient anatomy in conjunction a surgical procedure performed with a robotic device to reduce space constraints and simplify positioning of a patient positioner relative to the patient anatomy.

SUMMARY

Multifunctional holding devices for supporting both a robotic device and a patient positioner are provided, allowing improved positioning and/or supporting of patient anatomy in association with a surgical procedure.

In some embodiments, a holding device for securing a surgical robotic device and a patient anatomy positioner to a support is provided, the holding device comprising a carriage, an anchor component fixed to the carriage for attaching to the support, a patient stabilization connector extending from the anchor component for attaching to the patient positioner, and an elongate holder slidably mounted on the carriage for attaching to the robotic device, wherein, when the anchor component is attached to the support, the carriage and the patient stabilization connector are immobilized.

In some embodiments, a surgical holding device is provided, comprising a carriage, an anchor component fixed to the carriage for attaching to a support in an operating theater, a patient stabilization connector extending from the anchor component for attaching to a patient positioner, an elongate holder slidably mounted on the carriage for attaching to a horizontal linkage comprising at least one joint, wherein horizontal linkage is for attaching to a robotic device, and a hydraulic cylinder, wherein a first portion of the hydraulic cylinder is connected to the elongate holder and a second portion of the hydraulic cylinder is connected to the carriage, wherein, when the anchor component is attached to the support, the carriage and the patient stabilization connector are immobilized.

In some embodiments, a method of connecting a surgical robotic device and a patient anatomy positioner to a single position on a support is provided, comprising mounting the robotic device to an elongate holder, mounting the patient positioner to a patient stabilization connector, providing a carriage and slidably connecting the carriage to the elongate holder and fixedly connecting the carriage to the patient stabilization connector, connecting the carriage to an anchor component fixed to the carriage, and attaching to the anchor component to the support.

Further details of these various embodiments are described in more detail below.

DETAILED DESCRIPTION

Figure 1:
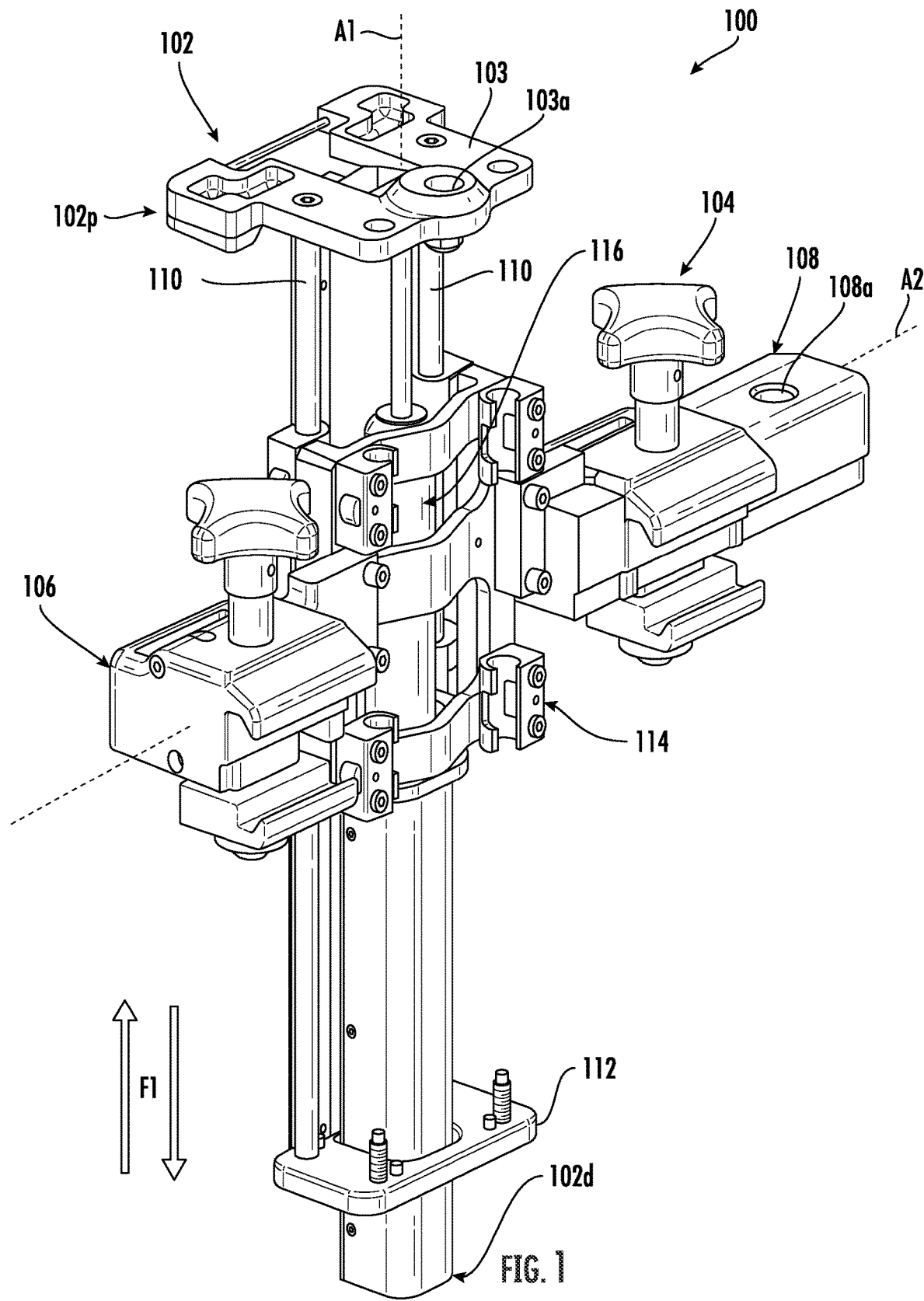
FIG. 1 is a perspective view of a multifunctional holding device.

FIG. 1 is a front perspective view of a multifunctional holding device 100. The holding device 100 may provide a compact solution for mounting both a robotic device and a patient positioner for stabilizing patient anatomy in an optimal or preferred position for a surgical procedure. For simplicity of illustration, the robotic device, the patient positioner, and the patient anatomy are not depicted. The holding device 100 may include an elongate holder 102 adapted to be adjustable in a longitudinal direction with respect to the axis A1. The elongate holder 102 may have a proximal end 102p and a distal end 102d. A mounting plate 103 having a bore 103a is provided on the elongate holder 102 on the proximal end 102p to directly couple to a surgical robotic device, or indirectly couple to the robotic device via a horizontal linkage (FIG. 11) interposed between the surgical robotic device and the mounting plate.

The elongate holder 102 may selectively translate longitudinally such that a vertical position of the proximal end 102p of the elongate holder may be adjusted relative to the stationary components of the holding device 100 (which will be described) and, accordingly, may be adjusted relative to an operating table with the bed rail (or other operating room structure). A vertical position of the robotic device coupled to the elongate holder 102 may be adjusted to a desired height relative to a patient on the operating table.

A second axis A2 (e.g., a lateral axis) is disposed perpendicular to the axis A1. The holding device 100 may include a first anchor component 104, a second anchor component 106, and a patient stabilization connector 108 adapted to be adjustable in a direction with respect to the axis A2. In some embodiments, the second anchor component 106 may be omitted.

The first anchor component 104 and the second anchor component 106 may engage a bed rail (not depicted) or other operating room structure oriented along an axis parallel to the axis A2. Such engagement may support (e.g., simultaneously support) the robotic device and the patient positioner (via the holding device 100), and moreover, in a predetermined spaced-apart lateral distance measured along the axis A2.

The patient stabilization connector 108 may extend laterally from the first anchor component 104 and has a socket 108a that may receive a patient positioner (e.g., a post of a patient positioner, said patient positioner comprising a pad for engaging the patient anatomy, an arm for support the pad, and a post for disposing in the socket to secure the patient positioner in place). Alternatively, the socket could be disposed on a plate of the patient positioner and the post could be part of the patient stabilization connector 108.

Returning to the elongate holder 102, a plurality of rails 110 extend between the mounting plate 103 and a base plate 112 adjacent to the distal end 102d of the elongate holder. The plurality of rails 110 are spaced apart and parallel to each other. In FIG. 1, the two foreground rails are removed for simplicity of illustration. Different numbers of rails in the plurality of rails 110 are contemplated. Preferably, there are at least two rails. The plurality of rails 110 define a space or channel 111 therebetween. In some embodiments, the mounting plate 103 and the base plate 112 define the proximal and distal bounds of the channel 111.

A carriage 114 may be slidably disposed in the channel 111 via engagement with the plurality of rails 110. Stated differently, if the carriage 114 is secured from longitudinal movement (such as by virtue of a connection to the first anchor component 104 and the second anchor component 106 which may be engaging a bed rail or other operating room structure), the elongate holder 102 may translate longitudinally along the axis A1 relative to the carriage and, accordingly, longitudinally relative to the anchor components and the patient stabilization connector 108 secured thereto. The elongate holder 102 may translate with application of a longitudinal force F1 (e.g., a translating adjusting force). The longitudinal force F1 may be applied by a user, such as a person, a robot, or an automated system.

A hydraulic cylinder 116 may be interposed between the mounting plate 103 and the carriage 114, e.g., at least partially within the channel 111 of the elongate holder 102.

In some embodiments, the hydraulic cylinder 116 may be configured such that, in the absence of the longitudinal force, the hydraulic cylinder will hold the elongate holder (and mounted robotic device) in place or position after application of the longitudinal force F1. In other words, without application of a force to the elongate holder 102 in the proximal or distal direction, the elongate holder may maintain its position relative to the stationary components (e.g., the carriage 114, the first anchor component 104, the second anchor component 106, and the patient stabilization connector 108) of the surgical holding device 100. The hydraulic cylinder 116 could be replaced with other locking arrangements, such as a cam clamp.

In some embodiments, the hydraulic cylinder 116, may (e.g., may also), at least in part, facilitate relative longitudinal translation of the elongate holder 102 relative to the carriage 114. The hydraulic cylinder 116 could be replaced with other lifting arrangements, such as a crank and screw. Alternatively, in another embodiment, coupled to suitable controls, the hydraulic cylinder 116 may provide the force to lift or lower the robotic device, at least in part.

As depicted, the first anchor component 104 and the patient stabilization connector 108 may be coupled to the carriage 114 on a first side of the carriage. The second anchor component 106 may be coupled to the carriage 114 on a second side of the carriage opposite the first side. The sides may be reversed, for example, to accommodate left-handed surgeons or a particular side of a patient or an operating table.

Figure 2:
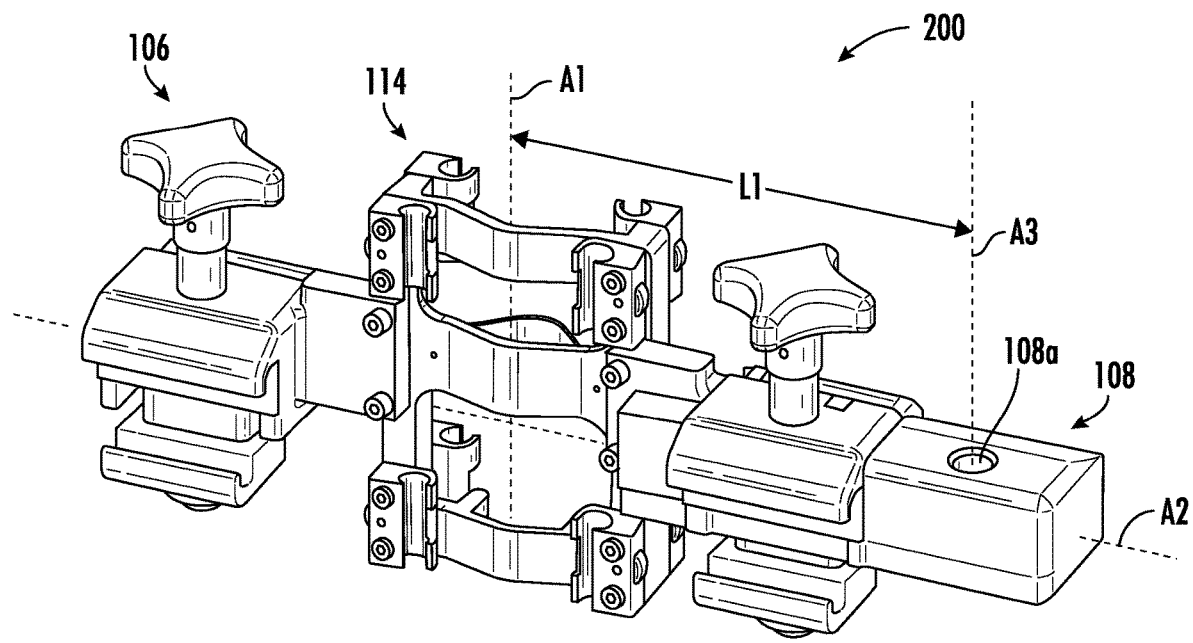
FIG. 2 is a perspective view of a subassembly of the holding device.

Turning to FIG. 2, a front perspective view, the second anchor component 106, the carriage 114, the first anchor component 104, and the patient stabilization connector 108 may define a subassembly 200 of the holding device. The subassembly 200 of the holding device 100 may be considered the stationary components of the holding device. It is understood that the term "subassembly" as used throughout this disclosure is not intended to be limiting in terms of manufacture, for example, the subassembly 200 could be assembled and then added to the elongate holder 102 (FIG. 1), or the carriage 114 may be attached to the plurality of rails 110 and then the first anchor component 104, the second anchor component 106, etc. attached to the carriage. The first anchor component 104, the second anchor component 106, and the patient stabilization connector 108 may all extend laterally from the carriage 114 along axis A2. The first anchor component 104, the second anchor component 106, and the patient stabilization connector 108 may all extend from the carriage 114 perpendicular to the axis A1.

The socket 108a may have a longitudinal axis A3 that may extend transverse to the lateral axis A2. A location or placement of the socket 108a relative to the longitudinal axis A1 of the elongate holder 102 may be based, at least in part, on one or more of an average patient anatomy and standard surgical procedure(s) performed with the robotic device. In some embodiments, the longitudinal axis A3 of the socket 108a may be perpendicular to the lateral axis A2 and parallel to the longitudinal axis A1 of the elongate holder 102.

As discussed above, it is a goal for the patient positioner received in the socket 108a to be close to the robotic device. A distance L1, as measured along the lateral axis A2, from the central longitudinal axis A1 of the elongate holder 102 (e.g., which may be co-axial with a central longitudinal axis of the carriage 114) to the longitudinal axis A3 of the socket 108a may be optimized. The distance L1 may be selected such that the patient positioner within the socket 108a may be located near the patient anatomy intended to be stabilized by the patient positioner upon insertion of the patient positioner into the socket 108a. Accordingly, once the patient positioner is received within the socket 108a, only minor adjustments to the positioning of the patient positioner relative to the patient anatomy may be necessary. In some embodiments, the patient stabilization connector 108 may translate laterally relative to the first anchor component 104 such that the distance L1 between the socket 108a and the longitudinal axis A1 of the elongate holder 102 may be adjustable.

Figure 3:
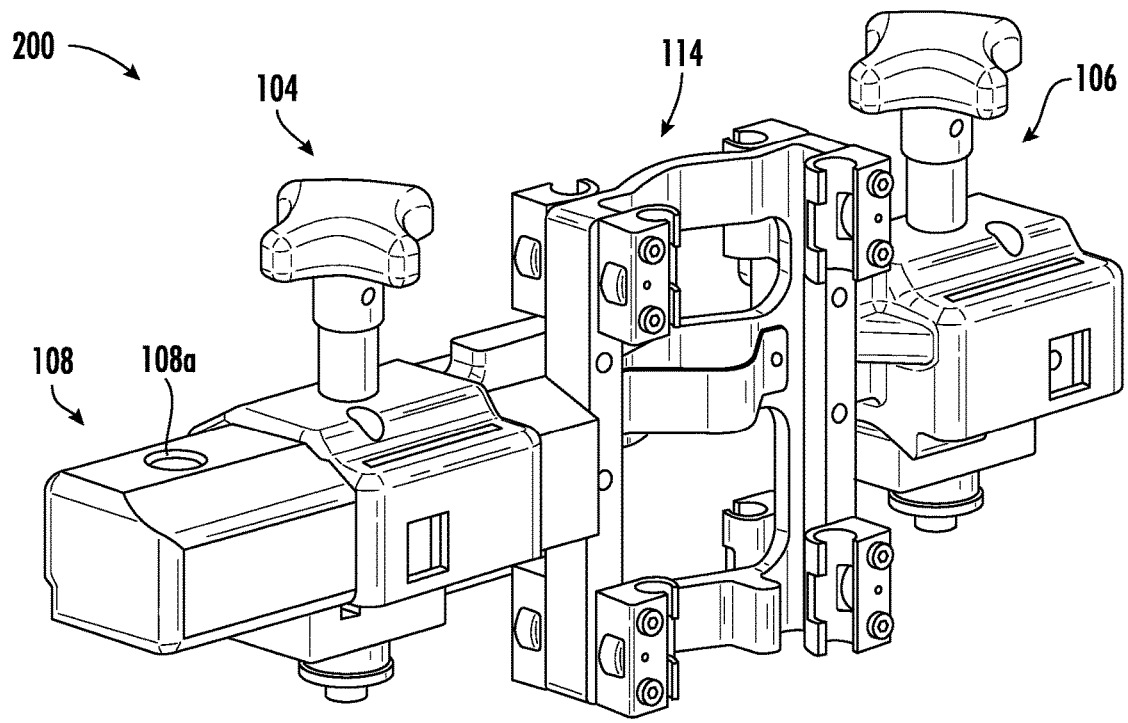
FIG. 3 is a perspective view of the subassembly of FIG. 2.

FIG. 3 is a rear perspective view of the subassembly 200 of FIG. 2.

Figure 4:
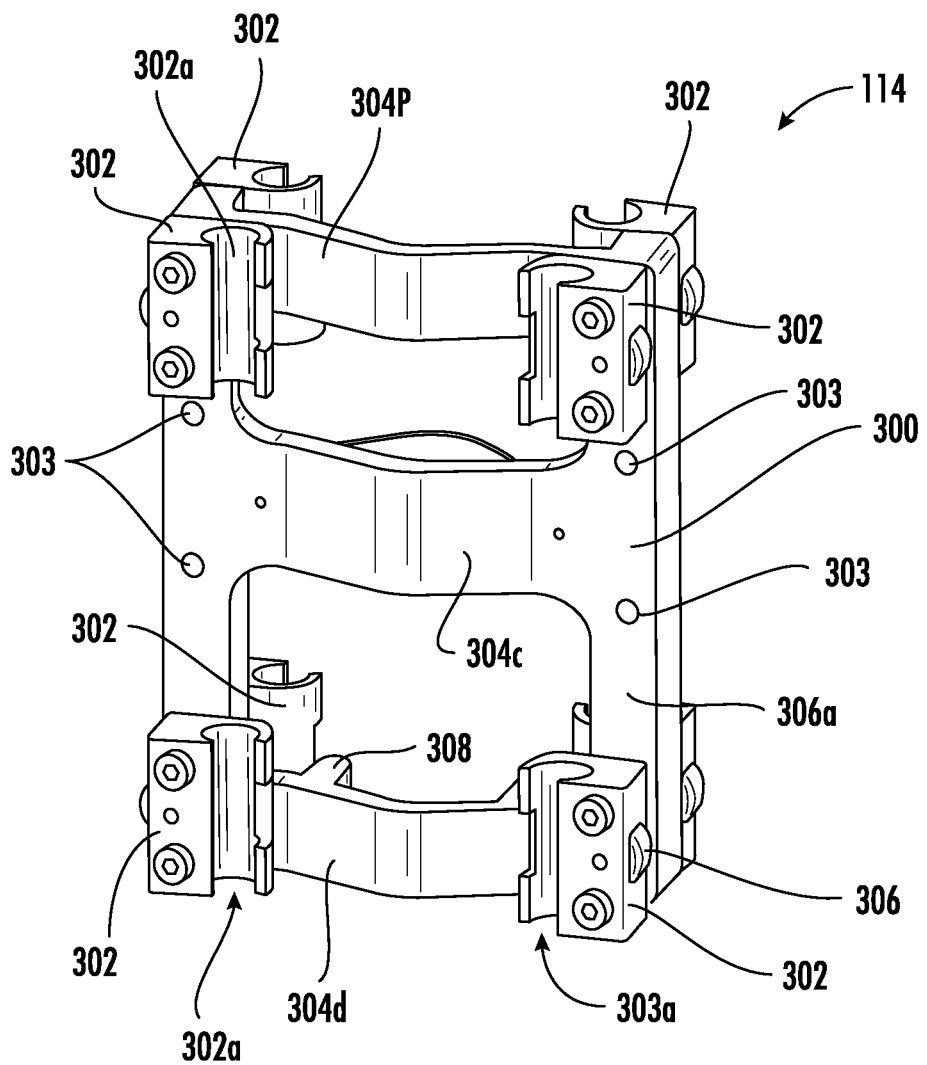
FIG. 4 is a perspective view of a carriage of the holding device.

FIG. 4 is a front perspective view of the carriage 114. The carriage 114 comprises a body 300. The body 300 may be generally rectangular in shape. With reference to the foregoing disclosure, the body 300 may have a proximal end, a distal end, a first anchor component side, and a second anchor component side (right, as illustrated). The body 300 may have a front surface (depicted) and a back surface (see FIGS. 3&15).

A plurality of rail receptacles 302 may be affixed to the body 300, e.g., bolted, welded, or otherwise securely affixed. Alternatively, the body 300 and the plurality of rail receptacles 302 may be formed as a unitary component. The plurality of rail receptacles 302 may be positioned the body 300 such that a longitudinally aligned pair of rail receptacles may slidably receive a portion of one of the plurality of rails 110 of the elongate holder 102. For example, each of the plurality of rail receptacles 302 may define a channel 302a for slidably engaging a rail portion. In some embodiments, one or more of the plurality of rail receptacles 302 may include a guide wheel 306 that may extend into the channel 302a. For example, the wheel 306 may abut the rail received within the channel 302a and may guide movement of the rail within the channel such that the longitudinal translation of the elongate holder 102 relative to the carriage 114 may be smooth and well controlled.

Openings 303 may be disposed in the body 300 to facilitate attachment of the first anchor component 104 and the second anchor component 106 on respective sides of the carriage 114.

The body 300 may define a plurality of struts 304 extending latitudinally across the body, such as a proximal strut 304p, a central strut 304c, and a distal strut 304d. The struts 304p, 304c, and 304d may brace or contact the hydraulic cylinder 116 (FIG. 1). For example, each strut 304p, 304c, 304d may have a concave portion that may contact an outer surface of the hydraulic cylinder 116. In some embodiments, the central strut 304c may have a complementary concave strut or portion on its opposite side to fully encircle the hydraulic cylinder 116. The distal strut 304d may include one or more bosses (or extensions) 308.

Figure 5:
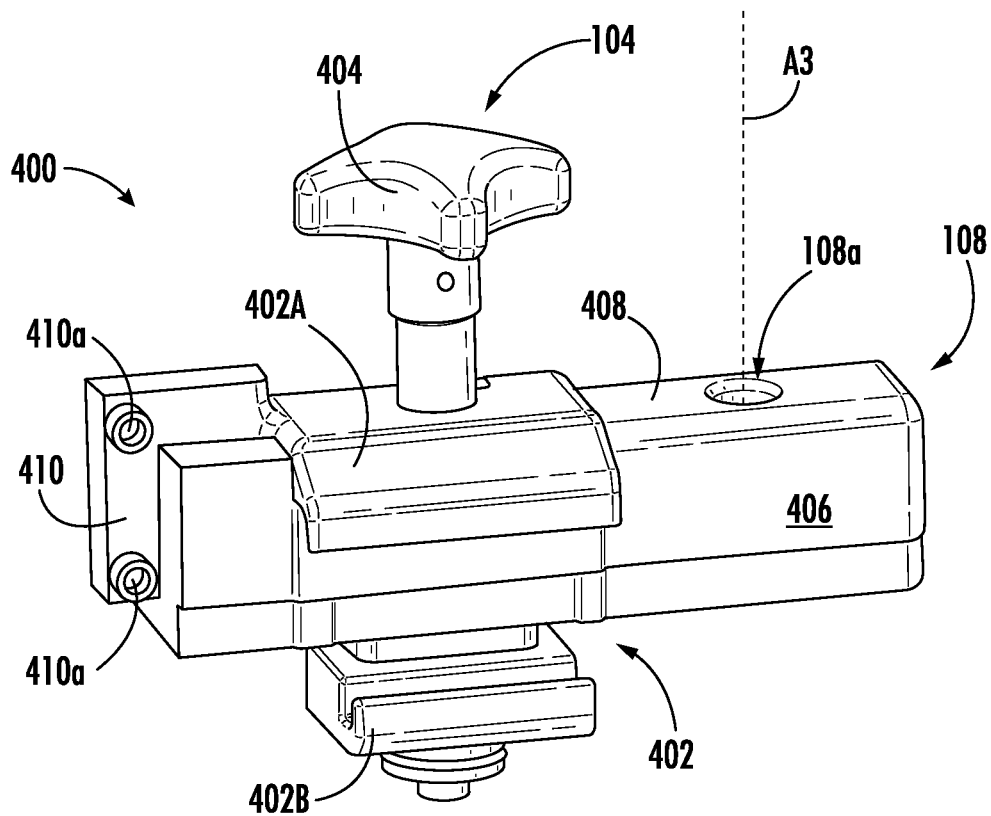
FIG. 5 is a perspective view of a subassembly of the holding device.

Turning to FIG. 5, a front perspective view, the first anchor component 104 and the patient stabilization connector 108 may define a subassembly 400 of the holding device. The subassembly 400 may be considered to be the components for attaching to a first side of the carriage 114 (FIG. 4). In some embodiments, the first anchor component 104 and the patient stabilization connector 108 may be formed as a unitary piece. However, preferably the first anchor component 104 and the patient stabilization connector 108 are separate pieces that may be securely attached to one another, for example, so that the patient connector 108 may translate laterally along the axis A2 to adjust the distance L1 (FIG. 2).

The first anchor component 104 may attach to the bed rail (or other operating room structure), and may be tightened to securely lock the anchor component to the bed rail. The first anchor component 104 may have an adjustable clamp 402 with a stationary jaw 402A and a movable jaw 402B defining a jaw opening extending therebetween. The movable jaw 402B may be translated using a knob 404 (e.g., the clamp 402 may be tightened or loosened). In operation, the first anchor component 104 may be placed such that the bed rail (or other operating room structure) is received within the jaw opening and the clamp 402 may then be tightened to secure and lock the bed rail between the stationary jaw 402A and the movable jaw 402B, such that relative movement between the bed rail and the first anchor component is prevented. The jaw opening of the clamp 402 is preconfigured to be adjustable to accommodate bed rails of various sizes.

The patient stabilization connector 108 may extend laterally from the first anchor component 104. A front surface 406 of the patient stabilization connector 108 may be disposed on the same side of the subassembly 400 as the opening of the clamp 402. As such, the front surface 406 may face towards, and, in some embodiments, may extend parallel to, the bed rail received within the jaw opening of the clamp 402. The socket 108a may extend through a top surface 408 of the patient stabilization connector 108. The socket 108a may receive a portion, for example a post, of the patient positioner, such that a pad portion of the patient positioner may extend over the operating table to contact and stabilize anatomy of a patient.

A mount plate 410 may extend from the first anchor component 104 or the patient stabilization connector 108 for attachment to the carriage body 114 with one or more fixation elements 410a, e.g., bolts, welds, or other attachment components. In some embodiments, the first anchor component 104 may translate along the patient stabilization connector 108 such that the position of the clamp 402 may be adjusted relative to the socket 108a and elongate holder 102. In such instances, the mount plate 410 may be integrally formed with the patient stabilization connector 108. Alternatively, the mount plate 410 may be integrally formed with the first anchor component 104, which may permit translation of the patient stabilization connector 108 relative to the carriage 114.

Figure 6:
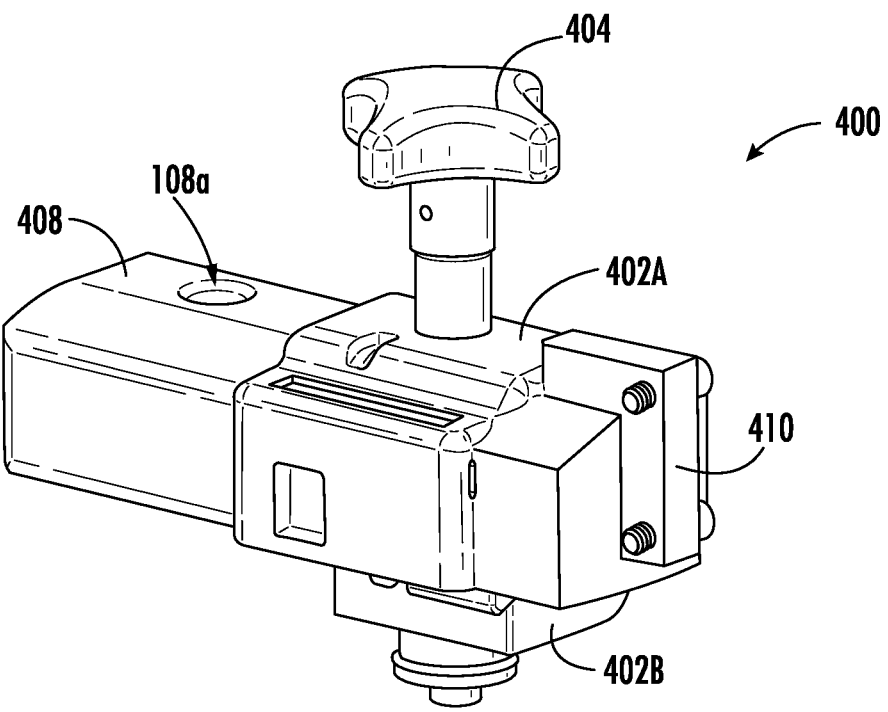
FIG. 6 is a rear perspective view of the subassembly of FIG. 5.

FIG. 6 is a rear perspective view of the subassembly 400 of FIG. 5.

Figure 7:
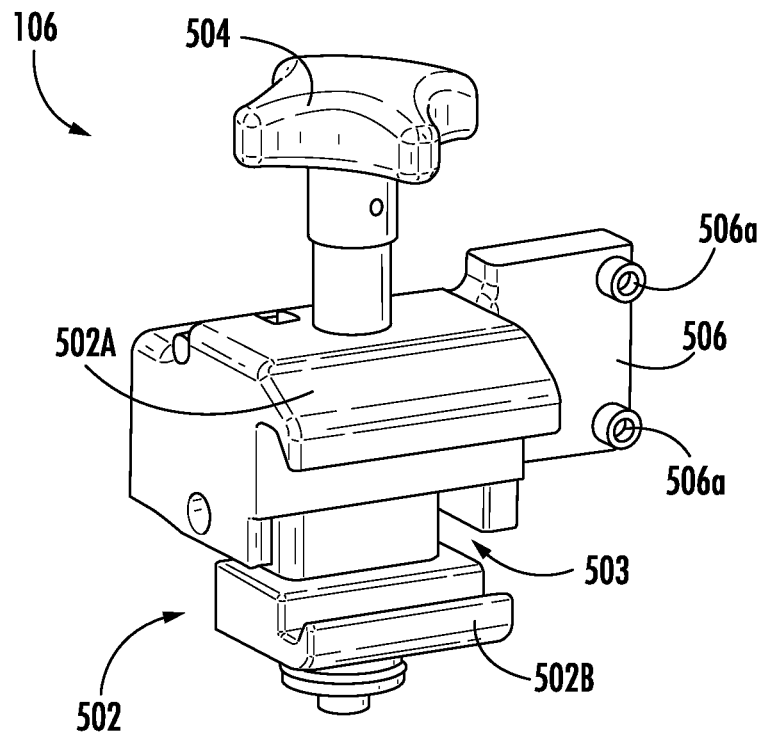
FIG. 7 is a perspective view of a second anchor component of the holding device.

FIG. 7 is a front perspective view of a second anchor component 106. As can be appreciated, as to clamping, the structure, operation, and use of the second anchor component 106 is similar or identical to that of the first anchor component 104. The second anchor component 106 may include a clamp 502 with a stationary jaw 502A, a movable jaw 502B, a clamp opening 503, and a knob 504. The bed rail (or other operating room structure) may be received within the clamp opening 503. The clamp 502 may be tightened (by turning the knob 504 to translate the moveable jaw 502B towards the stationary jaw 502A) to secure and lock the bed rail therein. The second anchor component 106 may include a mount plate 506. The mount plate 506 may attach to the carriage 114 via one or more fixation elements 506a, e.g., bolts, welds, or other attachment components.

Figure 8:
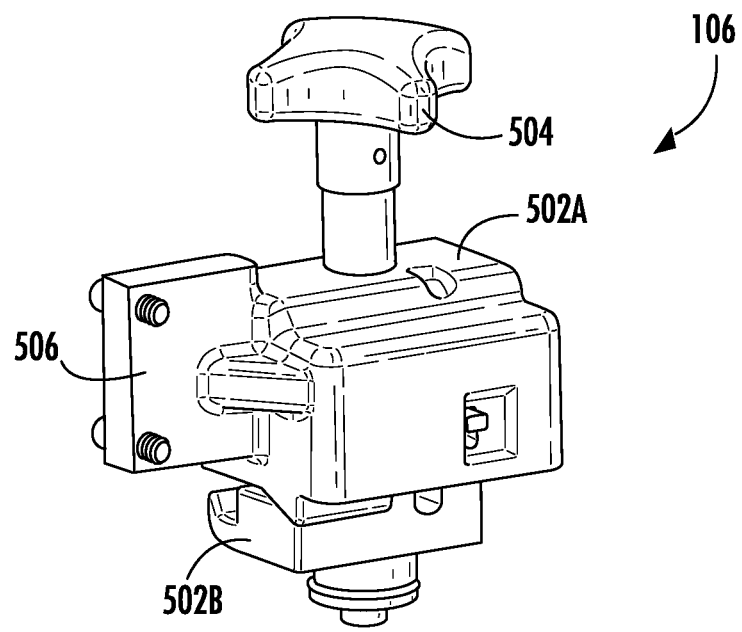
FIG. 8 is a rear perspective view of the second anchor component of FIG. 7.

FIG. 8 is a rear perspective view of the second anchor component 106.

Figure 9:
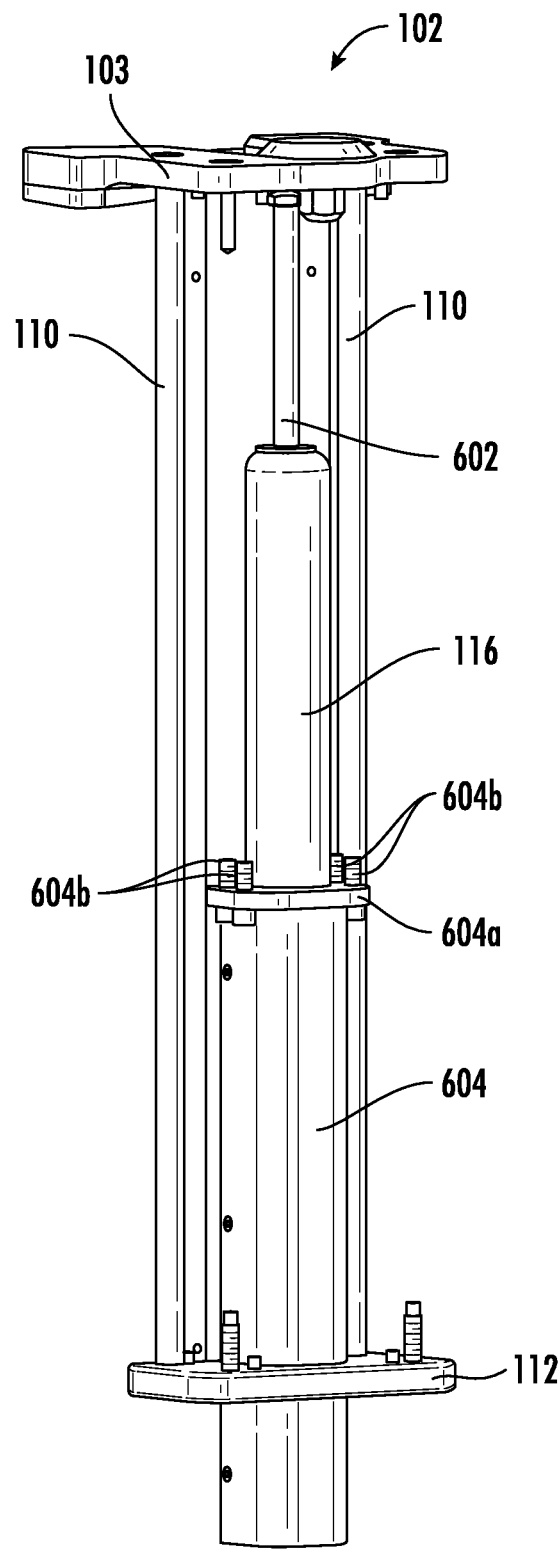
FIG. 9 is a perspective view of an elongate holder of the holding device.

FIG. 9 is a perspective view of the elongate holder 102 of the holding device (with a first cover plate removed). The hydraulic cylinder 116 may (e.g., may also), at least in part, facilitate relative longitudinal translation of the elongate holder 102 relative to the carriage. The hydraulic cylinder 116 may have a piston shaft 602 attached to the mounting plate 103.

The hydraulic cylinder 116 may have a base portion 604 which extends through an opening 609 (FIG. 10) in the base plate 112 of the elongate holder 102. Alternatively, the hydraulic cylinder 116 may be partially disposed inside the base portion 604. A top portion 604a of the base portion 604 is adapted to engage the carriage 114 via connectors 604b, such as screws, bolts, studs, etc. The top portion 604a may include a lip or flanged portion. As can be appreciated, if the carriage 114 is stationary (e.g., the anchor components are affixed to the bed rail), extension of the piston shaft will raise the mounting plate 103 (e.g., along with the plurality of rails 110 and base plate 112). The base plate 112 will translate with respect to the base portion 604.

Figure 10:
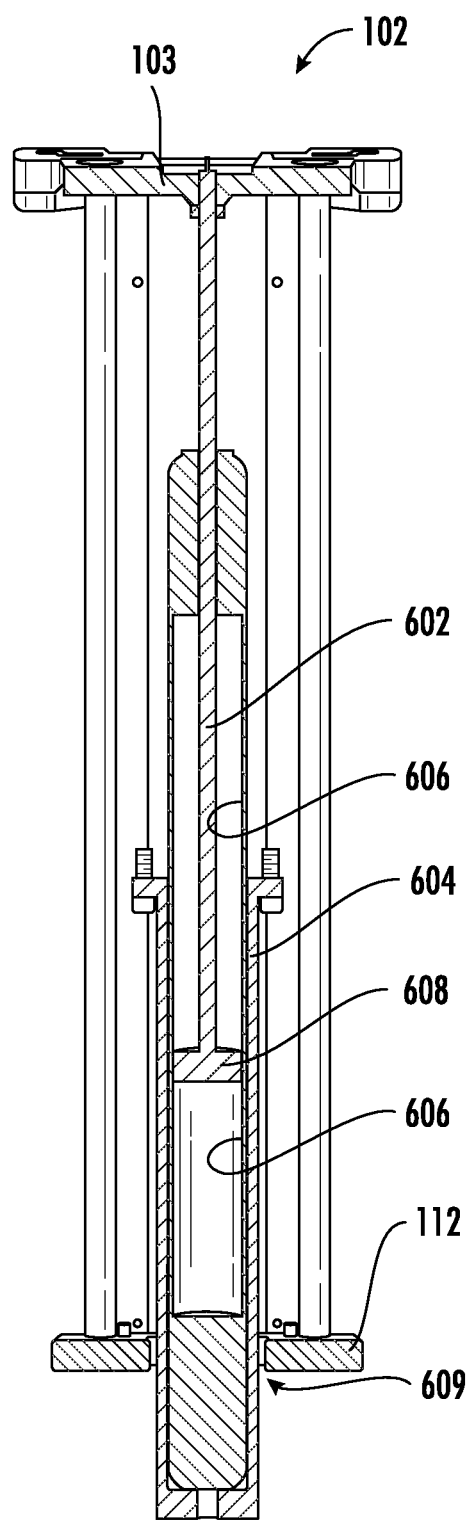
FIG. 10 is a cross-sectional view of FIG. 9.

Turning to FIG. 10, the base portion 604 may be a generally U-shaped component with an inner lumen that may extend longitudinally. The hydraulic cylinder 116 may be received within the inner lumen of the base portion 604, e.g., with a friction fit, such that relative motion between the hydraulic cylinder and the base may be prevented.

The hydraulic cylinder 116 may have a central piston cavity 606. The piston shaft 602 may extend distally and may terminate at a second end with a piston head 608 disposed in the piston cavity 606. The piston head 608 may translate longitudinally within the cavity 606 producing longitudinal motion of the piston shaft 602. The length of the cavity 606 may, at least in part, define a possible range of motion of the piston shaft 602 and thus a vertical range of motion of the robotic device.

The opening 609 in the base plate 112 of the elongate holder 102 allows the base plate (e.g., along with the mounting plate 103 and the plurality of rails 110) to translate with respect to the base portion 604 (e.g., which is fixed to the carriage 114).

In an example of operation, with the carriage 114 stationary, a translating (e.g., longitudinal) adjusting force (such as F1 of FIG. 1) may be applied proximally to the elongate holder 102, which may move the elongate holder, and the piston shaft 602 attached thereto, proximally relative to the hydraulic cylinder 116, the base portion 604, and the carriage 114. Alternatively, the longitudinal force F1 may be applied in the distal direction to the elongate holder 102, which may result in relative distal movement. Distances of travel may depend on stroke length of the hydraulic cylinder 116.

The hydraulic cylinder 116 may be constructed such that, in the absence of the longitudinal force, the piston head 608 may remain motionless relative to the hydraulic cylinder 116. In other words, without application of a force to the elongate holder 102 in the proximal or distal direction, the elongate holder 102 may maintain its position relative to the stationary components (e.g., the hydraulic cylinder 116, the base portion 604, the carriage 114, the first anchor component 104, the second anchor component 106, and the patient stabilization connector 108) of the surgical holding device 100. Alternatively, in another embodiment, coupled to suitable controls, the hydraulic cylinder 116 may (e.g., may also) provide the force to lift or lower the robotic device, at least in part.

Figure 11:
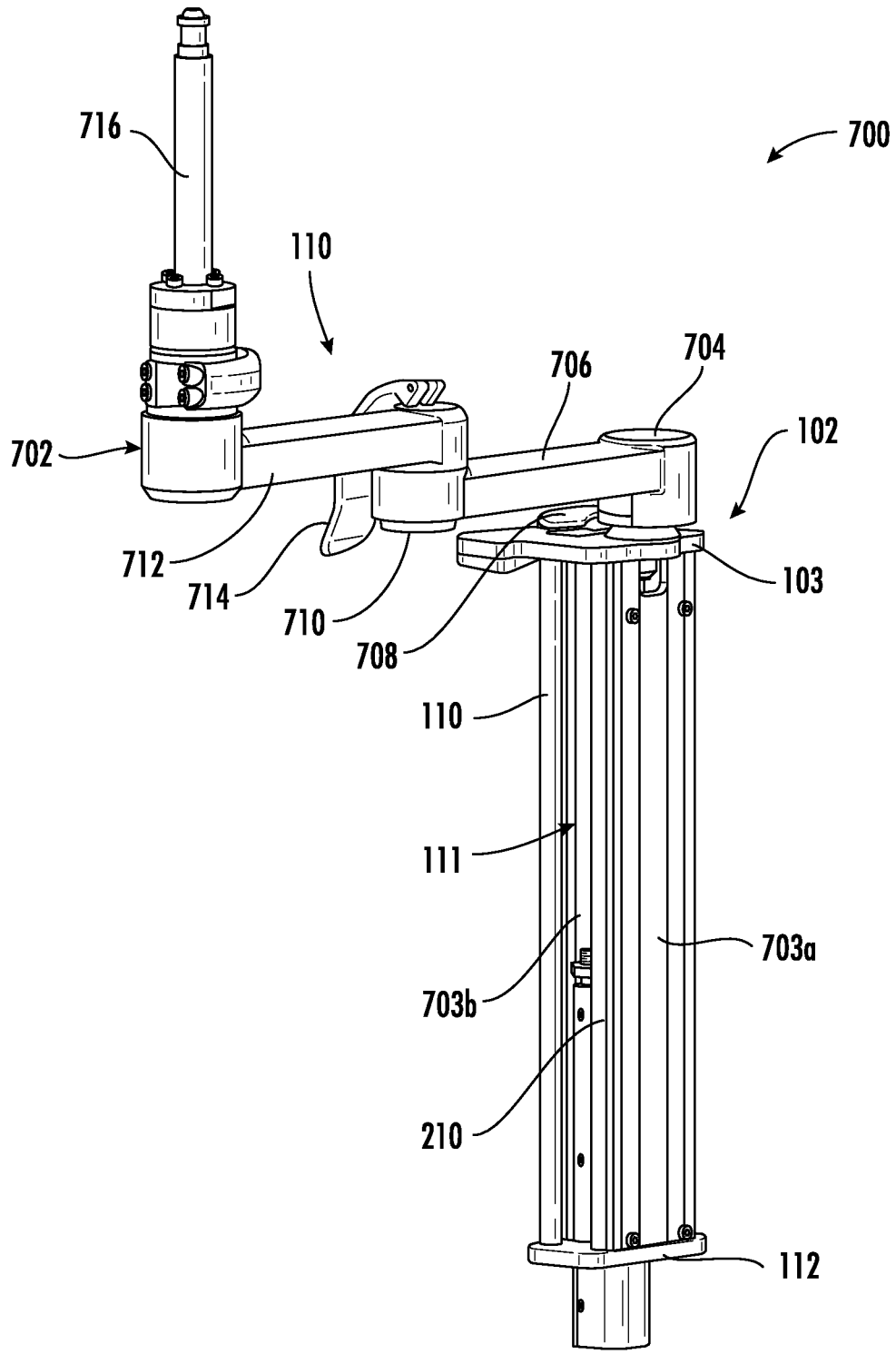
FIG. 11 is a perspective view of a subassembly of the holding device.

FIG. 11 is a perspective view of a subassembly 700 comprising the elongate holder 102 and an optional horizontal linkage 702. Stated differently, in some embodiments, a multifunctional holding device further comprises a horizontal linkage.

The elongate holder 102 may have a first cover plate 703a and a second cover plate 703b, e.g., to cover the hydraulic cylinder. The channel 111 is disposed between first cover plate 703a and a second cover plate 703b.

Figure 14:
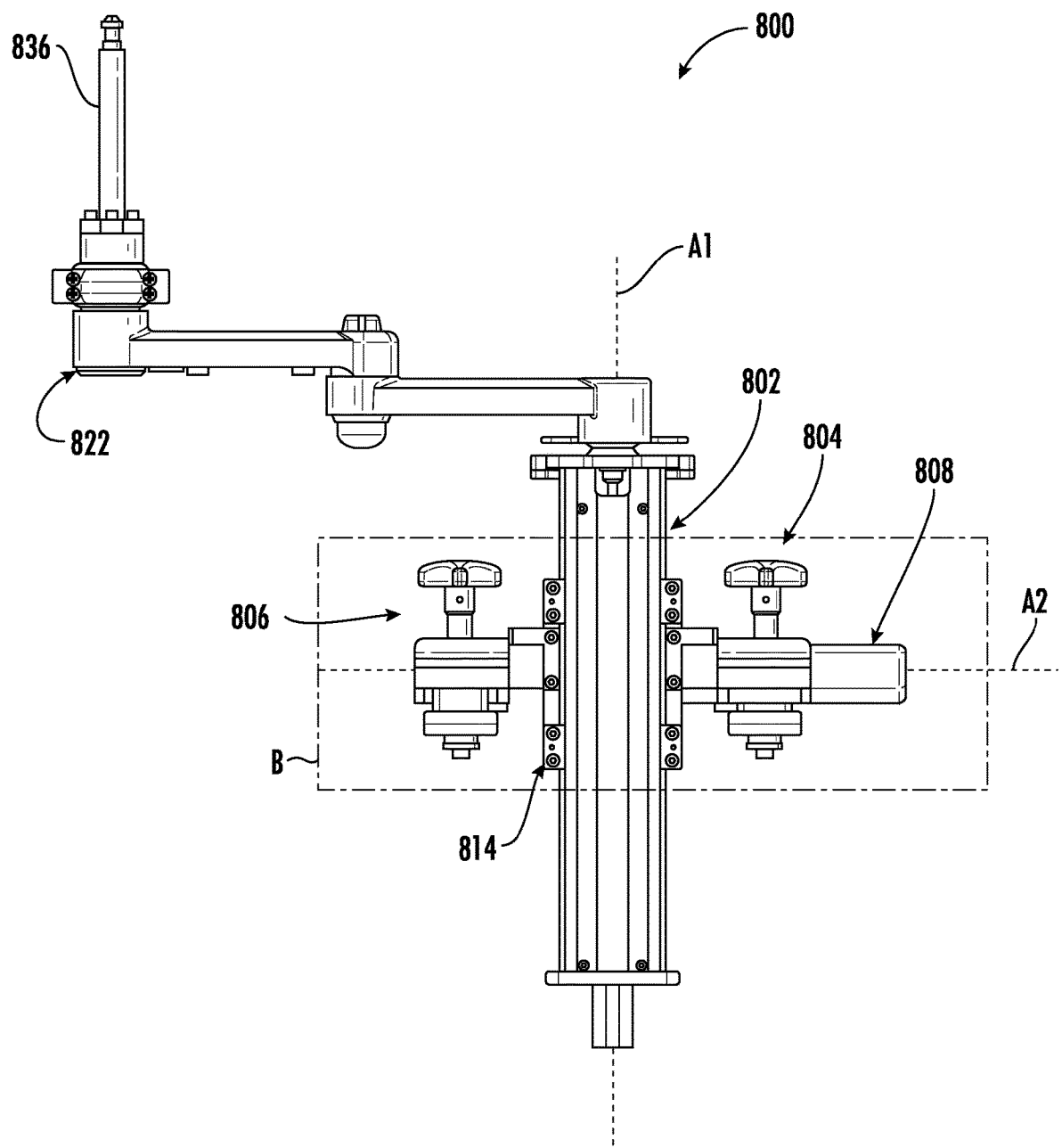
FIG. 14 is a front view of FIG. 12.

As depicted, the horizontal linkage 702 is attached to the mounting plate 103. A lockable pin joint 704 may connect a first articulable segment 706 of the horizontal linkage 702 to the mounting plate 103, such that the horizontal linkage may rotate relative to the elongate holder 102 about the longitudinal axis A1 (FIG. 14). The pin joint 704 may be selectively lockable, for example, a lever 708 may be placed in a first position to allow relative movement between the first segment 706 and the elongate holder 102 or in a second position to lock the pin joint and restrict relative movement between the first segment and the elongate holder.

A selectively lockable pin joint 710 may couple the first segment 706 to a second articulable segment 712 of the horizontal linkage 702, such that the first segment and the second segment may rotate relative to one another about a vertical axis of the joint. The pin joint 710 may be selectively lockable, for example, a lever 714 may be placed in a first position to allow relative movement between the first segment 706 and the second segment 712 or in a second position to lock the pin joint and restrict relative movement therebetween.

A robot mount 716 may extend longitudinally from a distal end of the second segment 712. The robot mount 716 may be configured to receive and retain the robotic device stably and securely. Although depicted as a post with a retaining groove, the robot mount 716 could be replaced with a port from receiving a fitting of the robotic device.

As can be appreciated, the joints 704 and 710 may be configured so that the horizontal linkage 702 may only move in a plane oriented parallel to the lateral axis A2 (FIG. 14). Accordingly, the robotic device may be adjusted laterally, e.g., after the first anchor component 104 and the second anchor component 106 are engaged. In fact, the horizontal linkage 702 may afford adjustment along a third axis of movement, e.g., forward or backward relative to the plane that would contain axis A1 and axis A2. Depending on the type of robotic device, this additional range of motion (e.g., compared to the holding device 100 (FIG. 1)) may be advantageous. In operation, the robotic device may be maneuvered to a desired position and then the levers 708 and 714 locked, e.g., a position of the robot mount 716 may be selectively adjustable and lockable relative to the elongate holder 102.

Figure 12:
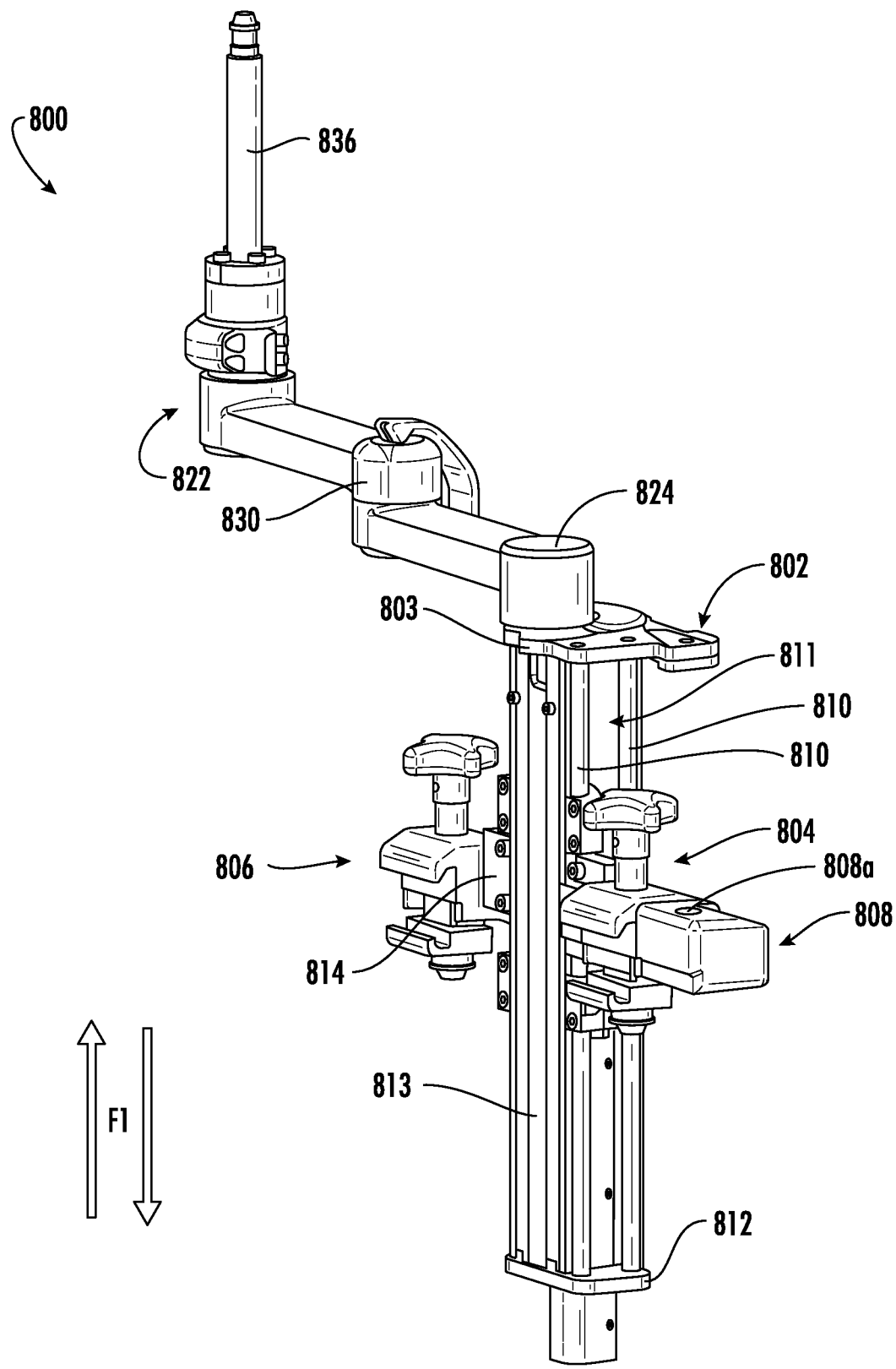
FIG. 12 shows a perspective view of another embodiment of a multifunctional holding device.

FIG. 12 shows a front perspective view of another embodiment of a multifunctional holding device, given the reference number 800. Features that are illustrated in FIG. 12 and not numbered (e.g., knobs, jaws, rail receptacles, etc.) are understood to be described above with respect to similarly named or illustrated components. The holding device 800 comprises an elongate holder 802 adapted to be longitudinally adjustable. The elongate holder 802 is adapted to be connected (in this case indirectly via the horizontal linkage 822) to a robotic device.

The holding device 800 comprises a group of stationary (as compared to the elongate holder) components: a first anchor component 804, a second anchor component 806, and a patient stabilization connector 808 secured to, and extending laterally from, the first anchor component. The elongate holder 802 may translate proximally (or distally) with respect to the stationary components with application of a longitudinal force F1 (e.g., a translating adjusting force). The longitudinal force F1 may be applied by a user, such as a person, a robot, or an automated system. In the absence of the longitudinal force F1, the elongate holder 802 may be configured to remain motionless (such as by action of a hydraulic cylinder or other components for preventing translation).

The patient stabilization connector 808 has a socket 808*a* that may receive a patient positioner (e.g., a post of a patient positioner, said patient positioner comprising a pad for engaging the patient anatomy, an arm for support the pad, and a post for disposing in the socket to secure the patient positioner in place). Alternatively, the socket could be disposed on a plate of the patient positioner and the post could be part of the patient stabilization connector 808. The socket 808*a* may have a longitudinal axis that may extend transverse to the lateral axis A2 (FIG. 14). A location or placement of the socket 808*a* relative to a longitudinal axis of the elongate holder 802 may be based, at least in part, on one or more of an average patient anatomy and standard surgical procedure(s) performed with the robotic device. The patient positioner received in the socket 808*a* may need to be close to the robotic device, e.g., selected such that the patient positioner retained within the socket may be located near the patient anatomy intended to be stabilized by the patient positioner. Only minor adjustments to the positioning of the patient positioner relative to the patient anatomy may be necessary. In some embodiments, the patient stabilization connector 808 may translate laterally relative to the first anchor component 804 such that a distance between the socket 808*a* and the longitudinal axis A1 (FIGS. 13, 14) of the elongate holder 802 may be adjustable. The patient stabilization connector 808 may be locked in place after adjustment.

The elongate holder 802 comprises a plurality of rails 810 that are spaced apart and parallel to each other. The plurality of rails 810 define a space or channel 811 therebetween. The plurality of rails 810 extend between a mounting plate 803 and a base plate 812 adjacent to a distal end of the elongate holder. The elongate holder 802 may further comprise a cover plate 813.

A carriage 814 may extend across the channel 811. The carriage 814 comprises a plurality of rail receptacles, such that a longitudinally aligned pair of rail receptacles may slidably receive a portion of one of the plurality of rails 810. For example, four rails 810 may require four pairs of rail receptacles, e.g., eight rail receptacles (four rail receptacles on a front of the carriage and four rail receptacles on a front of the carriage). The carriage 814 may be connected to the second anchor component 806 on a first side (for example, interposed between a longitudinally aligned pair of rail receptacles), and may be connected to the first anchor component 804 and the patient stabilization connector 808 on a side opposite the first side (for example, interposed between a longitudinally aligned pair of rail receptacles), such that the first anchor component 804, the second anchor component 806, and the patient stabilization connector 808 extend laterally from the carriage 814, and perpendicular or substantially perpendicular to the elongate holder 802.

Although not visible in FIG. 12, a hydraulic cylinder may also be disposed at least partially within the channel 811. A first portion of the hydraulic cylinder may be secured to the elongate holder 802 and a second portion of the hydraulic cylinder may be secured to the carriage 814. When the anchor components 804, 806 are secured to a bed rail (or other operating room structure), the carriage 814 will necessarily be stationary. The longitudinal force F1 may be applied proximally (or distally) to the elongate holder 802, which may move the elongate holder (and the first portion of the hydraulic cylinder). The hydraulic cylinder may exert a holding force, such that, in the absence of the force F1 (e.g., proximal or distal) being applied to the elongate holder 802, the elongate holder may maintain its position relative to the stationary components (e.g., the carriage 814, the first anchor component 804, the second anchor component 806, and the patient stabilization connector 808) of the surgical holding device 800. The hydraulic cylinder may be configured to counter the weight of the elongate holder 802, the robotic device, and a horizontal linkage 822 attached to the mounting plate 803 (e.g., in order to hold those components in position). The hydraulic cylinder may be configured to have a relatively strong holding force, but be moved by a relatively small force F1 to allow smooth operation. For example, coupled to suitable controls, the hydraulic cylinder may (e.g., may also) provide the force to lift or lower the robotic device, at least in part.

Figure 13:
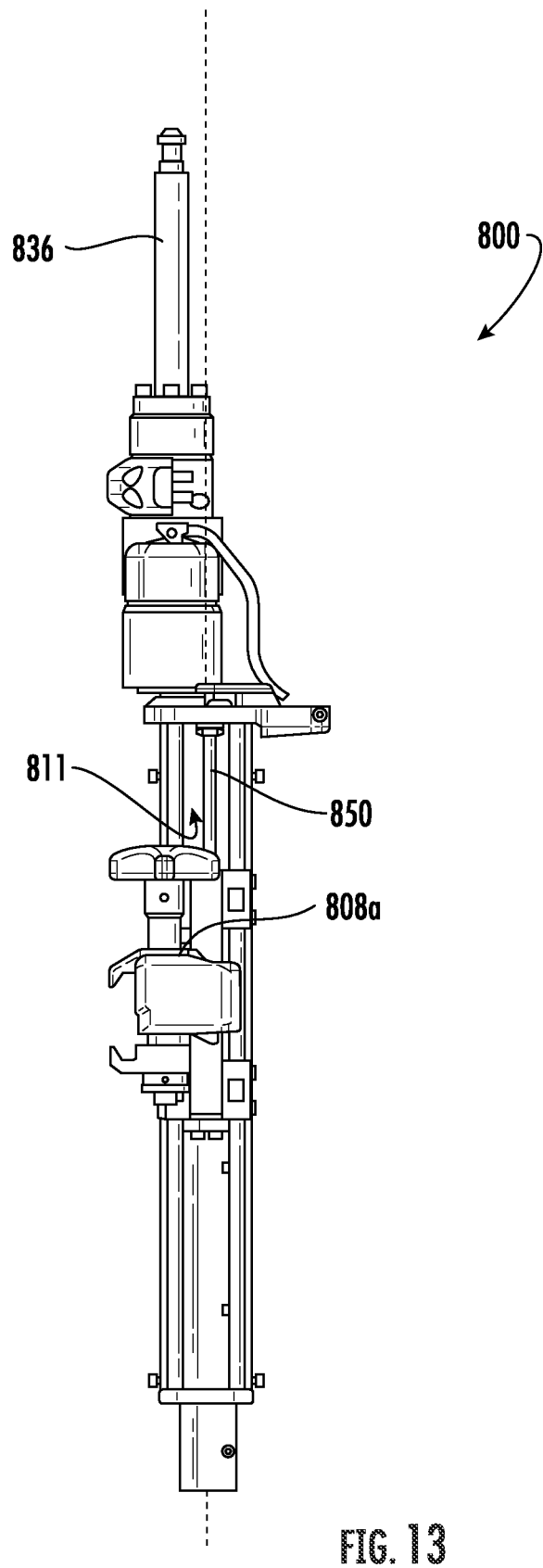
FIG. 13 is a side view of FIG. 12.

A lockable pin joint 824 may connect a first articulable segment of the horizontal linkage 822 to the mounting plate 803, such that the horizontal linkage may rotate relative to the elongate holder 802 about a longitudinal axis A1 (FIGS. 13, 14). The pin joint 824 may be selectively lockable, for example, a lever may be placed in a first position to allow relative movement between the first segment and the elongate holder 802 or in a second position to lock the pin joint and restrict relative movement between the first segment and the elongate holder.

A selectively lockable pin joint 830 may couple the first segment to a second articulable segment of the horizontal linkage 822, such that the first segment and the second segment may rotate relative to one another about a vertical axis of the joint. The pin joint 830 may be selectively lockable, for example, a lever may be placed in a first position to allow relative movement between the first segment and the second segment or in a second position to lock the pin joint and restrict relative movement therebetween.

A robot mount 836 may extend longitudinally from a distal end of the second segment of the horizontal linkage 822. The robot mount 836 may be configured to receive and retain the robotic device stably and securely. Although depicted as a post with a retaining groove, the robot mount 836 could be replaced with a port from receiving a fitting of the robotic device.

As can be appreciated, the joints 824 and 830 may be configured so that the horizontal linkage 802 may only move in a plane oriented parallel to the lateral axis A2 (FIG. 14). Accordingly, the robotic device may be adjusted laterally, e.g., after the first anchor component 804 and the second anchor component 806 are engaged. In fact, the horizontal linkage 802 may afford adjustment along a third axis of movement, e.g., forward or backward relative to the plane that would contain axis A1 (FIGS. 13, 14) and axis A2 (FIG. 14). Depending on the type of robotic device, this additional range of motion (e.g., compared to the holding device 100 (FIG. 1)) may be advantageous. In operation, the robotic device may be maneuvered to a desired position and then the joints 824 and 830 locked, e.g., a position of the robot mount 836 may be selectively adjustable and lockable relative to the elongate holder 802.

FIG. 13 is a side view of FIG. 12. The robot mount 836 and the socket 808a may have parallel axes. In some embodiments, it may be desirable to have the hydraulic piston (if present) disposed in the channel 811 and its piston aligned with the axis A1, e.g., parallel to one or more of an axis of the robot mount 836 and/or an axis of the socket 808a.

Figure 15:
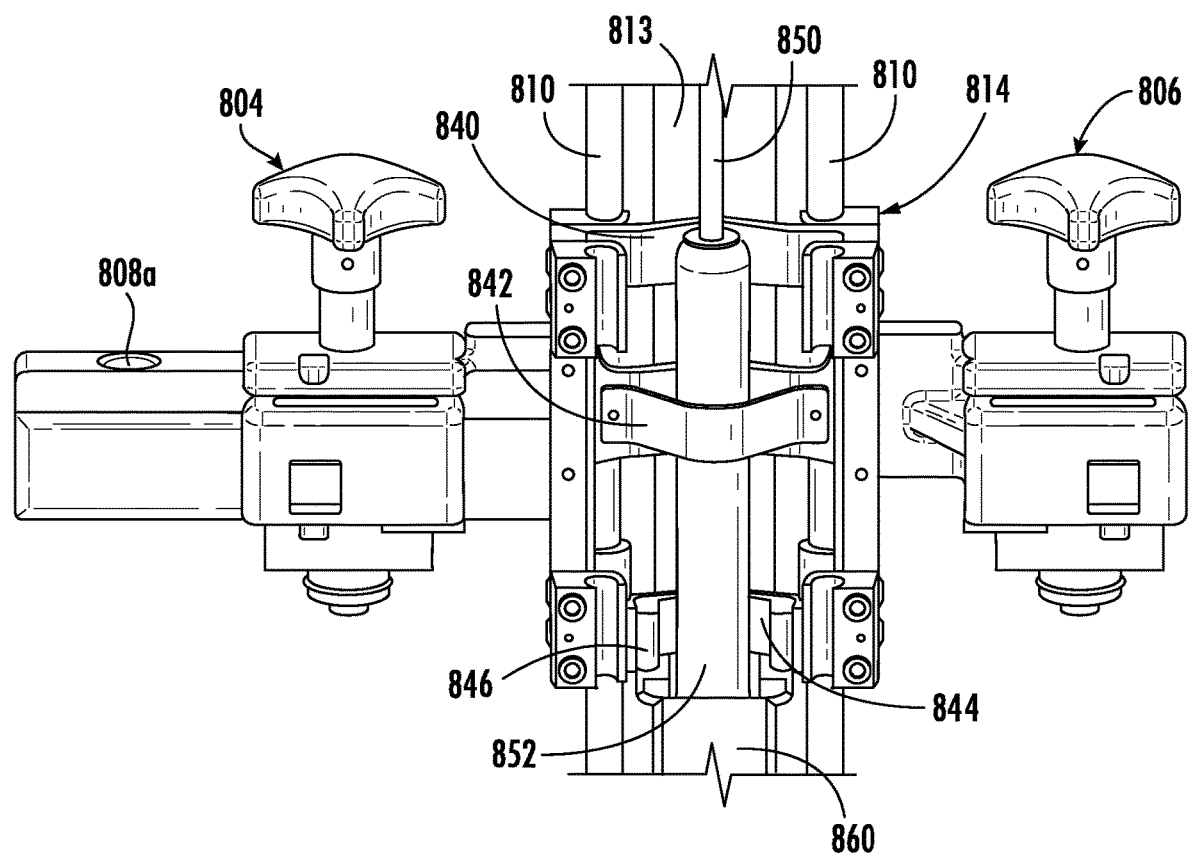
FIG. 15 is a rear detail view of area B of FIG. 14.

FIG. 14 is a front view of FIG. 12, and FIG. 15 is a rear detail view of area B of FIG. 14. Turning to FIG. 15, the first anchor component 804, the second anchor component 806, and the patient stabilization connector 808 having the socket 808a, and the carriage 814 are shown. The front two of the plurality of rails 810 and cover plate 813 are illustrated, but the back two rails (which would be closest in the figure, as this is a rear view) and a rear cover plate are removed to simplify the drawing.

The hydraulic cylinder 852 is disposed at least partially within the channel. A piston shaft 850 extends from the hydraulic cylinder 852 and is connected to the mounting plate (not visible). The hydraulic cylinder 852 is engaged with a base 860. The base 860 is secured to the carriage 814.

The carriage 814 has a plurality of struts for engaging the hydraulic cylinder 852 (but not the piston shaft 850). A proximal strut 840 is disposed toward the front of the device 800. A central strut 842 is disposed toward the back. A distal strut 844 has a boss 846, which may abut a cover plate (e.g., a lip or flanged portion of the cover plate) and/or receive connectors to secure the carriage 814 to the base 860.

In using the holding device 800 in a surgical environment, it may be important to create and maintain a sterile barrier between the sterile surgical operating space and the holding device.

Figure 16:
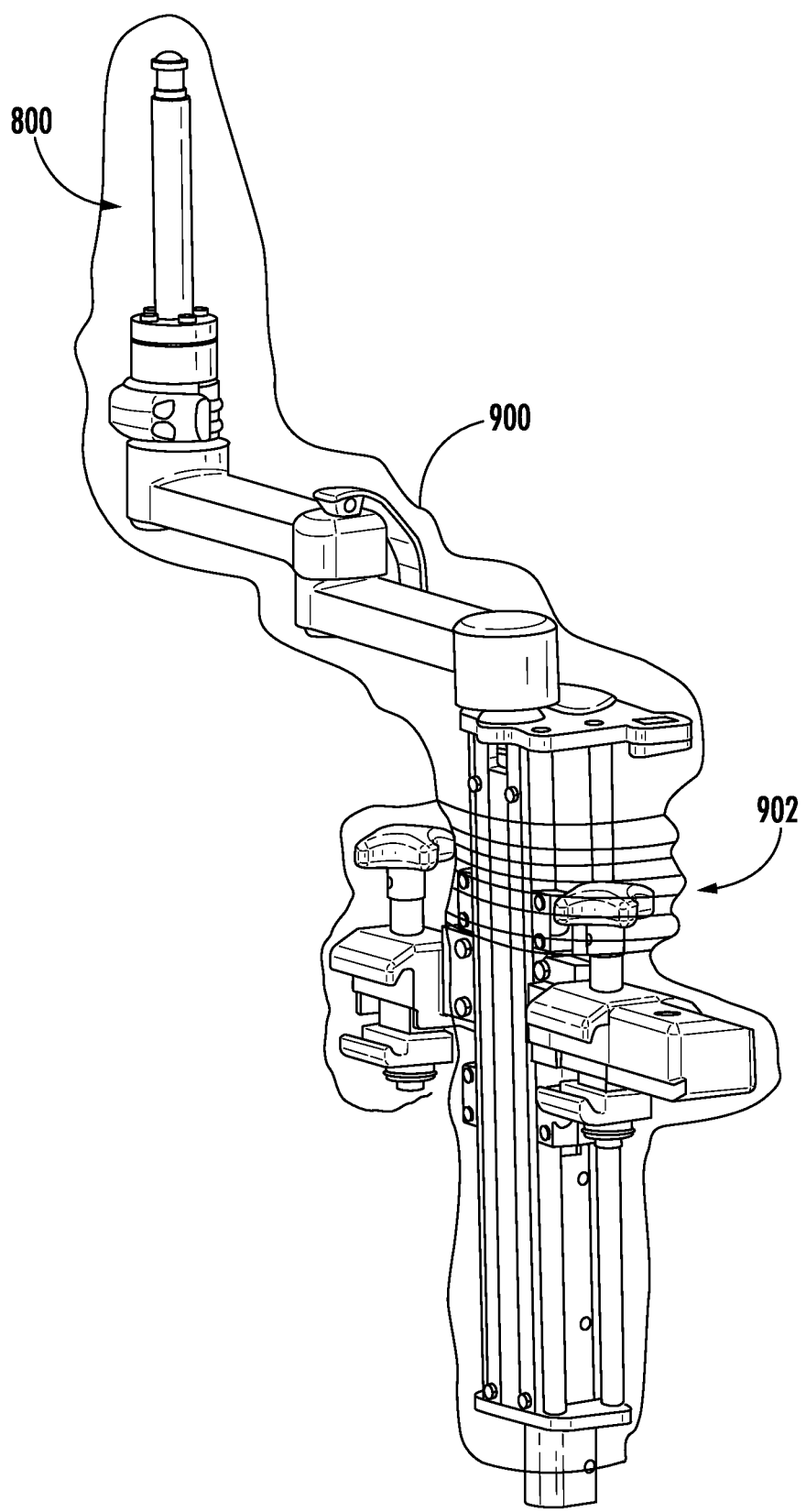
FIG. 16 is a perspective view of the holding device of FIG. 12 with a drape.

FIG. 16 shows the holding device of FIG. 12 with a surgical drape 900 that may be placed over the holding device 800 to create a sterile barrier and maintain a sterile operating space. The drape 900 may be secured to the holding device 800 with one or more ties or other fasteners (not shown). A portion 902 of the surgical drape 900 may extend over the elongate holder 802. In some embodiments, the portion 902 may be made from a stronger material and/or may include one or more expansion features, such as accordion folds, such that the elongate holder 802 may translate longitudinally without tearing the drape.

Further, in some embodiments, the drape 900 may be designed to extend into or through the patient positioning socket 808a of the patient stabilization connector 108. It is understood that the patient positioner (not depicted) may have a separate sterile drape that may be received within the patient positioning socket 808a along with the positioner. Accordingly, a sterile barrier may be maintained between the sterile operating space and the holding device 800 and patient positioner, respectively.

Figure 17:
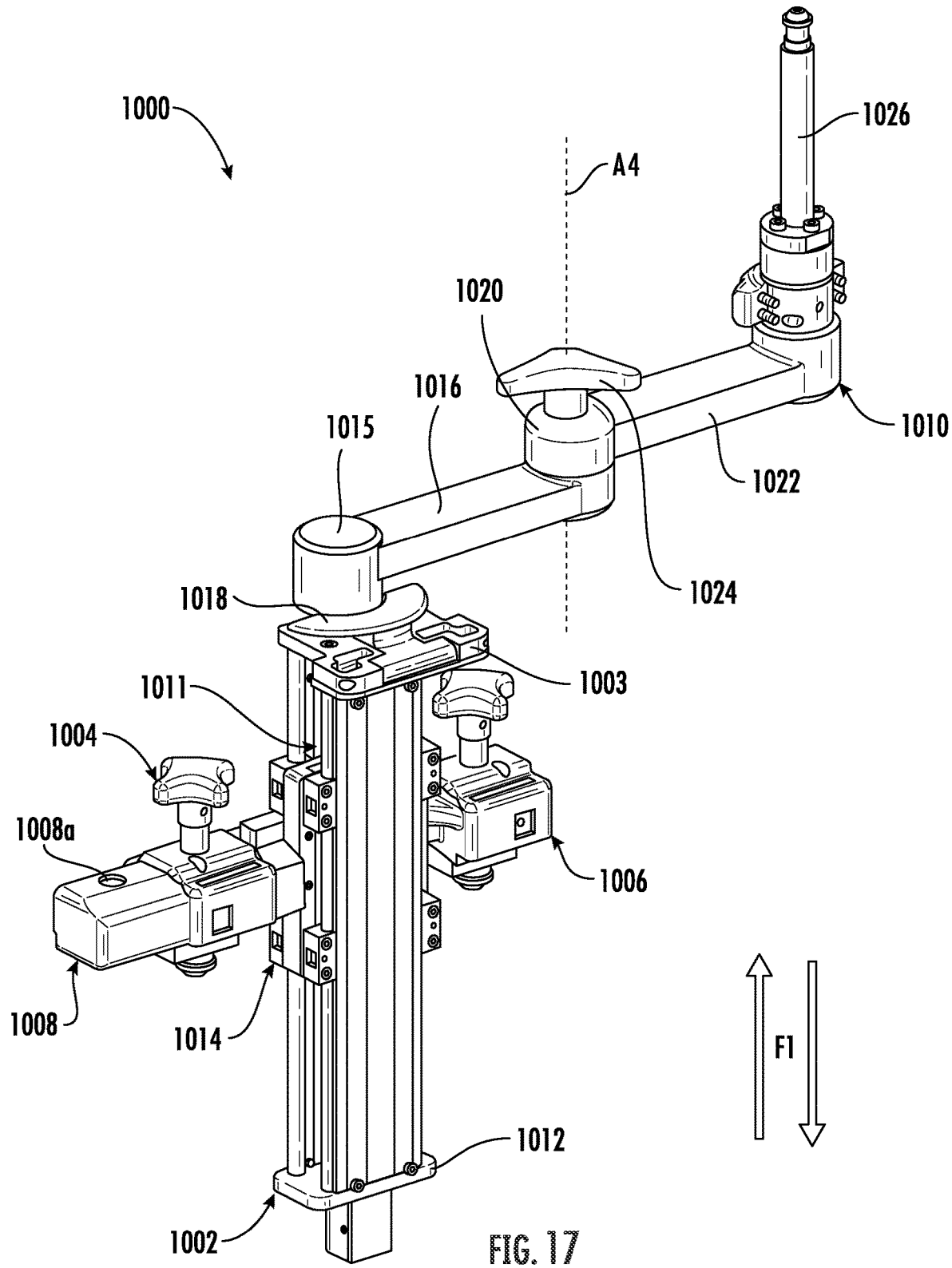
FIG. 17 is a perspective view of yet another embodiment of a multifunctional holding device.

FIG. 17 is a rear perspective view of another embodiment of a multifunctional holding device, given the reference number 1000. Features that are illustrated in FIG. 17 and not numbered (e.g., knobs, jaws, rail receptacles, etc.) are understood to be described above with respect to similarly named or illustrated components. The holding device 1000 comprises an elongate holder 1002 adapted to be longitudinally adjustable. The elongate holder 1002 is adapted to be connected (in this case indirectly via the horizontal linkage 1010) to a robotic device.

The holding device 1000 comprises a group of stationary (as compared to the elongate holder) components: a first anchor component 1004, a second anchor component 1006, and a patient stabilization connector 1008 secured to, and extending laterally from, the first anchor component. The elongate holder 1002 may translate proximally (or distally) with respect to the stationary components with application of a longitudinal force F1 (e.g., a translating adjusting force). The longitudinal force F1 may be applied by a user, such as a person, a robot, or an automated system. In the absence of the longitudinal force F1, the elongate holder 1002 may be configured to remain motionless (such as by action of a hydraulic cylinder or other components for preventing translation).

The patient stabilization connector 1008 has a socket 1008a that may receive a patient positioner (e.g., a post of a patient positioner, said patient positioner comprising a pad for engaging the patient anatomy, an arm for support the pad, and a post for disposing in the socket to secure the patient positioner in place). Alternatively, the socket could be disposed on a plate of the patient positioner and the post could be part of the patient stabilization connector 1008. The socket 1008a may have a longitudinal axis and location or placement of the socket 1008a relative to a longitudinal axis of the elongate holder 1002 may be based, at least in part, on one or more of an average patient anatomy and standard surgical procedure(s) performed with the robotic device. The patient positioner received in the socket 1008a may need to be close to the robotic device, e.g., selected such that the patient positioner retained within the socket may be located near the patient anatomy intended to be stabilized by the patient positioner. Only minor adjustments to the positioning of the patient positioner relative to the patient anatomy may be necessary. In some embodiments, the patient stabilization connector 1008 may translate laterally relative to the first anchor component 1004 such that a distance between the socket 1008a and the longitudinal axis of the elongate holder 1002 may be adjustable. The patient stabilization connector 1008 may be locked in place after adjustment.

The elongate holder 1002 comprises a plurality of rails that are spaced apart and parallel to each other defining a space or channel 1011 therebetween. The plurality of rails extend between a mounting plate 1003 and a base plate 1012 adjacent to a distal end of the elongate holder 1002. The elongate holder 1002 may further comprise a cover plate.

A carriage 1014 may extend across the channel 1011. The carriage 1014 comprises a plurality of rail receptacles, such that a longitudinally aligned pair of rail receptacles may slidably receive a portion of one of the plurality of rails. The carriage 1014 may be connected to the second anchor component 1006 on a first side (for example, interposed between a longitudinally aligned pair of rail receptacles), and may be connected to the first anchor component 1004 and the patient stabilization connector 1008 on a side opposite the first side (for example, interposed between a longitudinally aligned pair of rail receptacles), such that the first anchor component 1004, the second anchor component 1006, and the patient stabilization connector 1008 extend laterally from the carriage 1014, and perpendicular or substantially perpendicular to the elongate holder 1002.

Although not visible in FIG. 17, a hydraulic cylinder may also be disposed at least partially within the channel 1011. A first portion of the hydraulic cylinder may be secured to the elongate holder 1002 and a second portion of the hydraulic cylinder may be secured to the carriage 1014. When the anchor components 1004, 1006 are secured to a bed rail (or other operating room structure), the carriage

1014 will necessarily be stationary. The longitudinal force F1 may be applied proximally (or distally) to the elongate holder 1002, which may move the elongate holder (and the first portion of the hydraulic cylinder). The hydraulic cylinder may exert a holding force, such that, in the absence of the force F1 (e.g., proximal or distal) being applied to the elongate holder 1002, the elongate holder may maintain its position relative to the stationary components (e.g., the carriage 1014, the first anchor component 1004, the second anchor component 1006, and the patient stabilization connector 1008) of the surgical holding device 1000. The hydraulic cylinder may be configured to counter the weight of the elongate holder 1002, the robotic device, and a horizontal linkage 1010 attached to the mounting plate 1003 (e.g., in order to hold those components in position). The hydraulic cylinder may be configured to have a relatively strong holding force, but be moved by a relatively small force F1 to allow smooth operation. For example, coupled to suitable controls, the hydraulic cylinder may (e.g., may also) provide the force to lift or lower the robotic device, at least in part.

A lockable pin joint 1015 may connect a first articulable segment 1016 of the horizontal linkage 1010 to the mounting plate 1003, such that the horizontal linkage may rotate relative to the elongate holder 1002 about a longitudinal axis. The pin joint 1015 may be selectively lockable, for example, a lever 1018 may be placed in a first position to allow relative movement between the first segment and the elongate holder 1002 or in a second position to lock the pin joint and restrict relative movement between the first segment and the elongate holder.

A selectively lockable pin joint 1020 may couple the first segment 1016 to a second articulable segment 1022 of the horizontal linkage 1010, such that the first segment and the second segment may rotate relative to one another about a vertical axis A4 of the joint. The pin joint 1020 may be selectively lockable, for example, a knob 1024 may be rotated to a first position to allow relative movement between the first segment 1016 and the second segment 1022 or the knob may be rotated (e.g., tightened) to a second position to lock the pin joint and restrict relative movement between the first segment and the second segment.

A robot mount 1026 may extend longitudinally from a distal end of the second segment 1022 of the horizontal linkage 1010. The robot mount 1036 may be configured to receive and retain the robotic device stably and securely. Although depicted as a post with a retaining groove, the robot mount 1026 could be replaced with a port from receiving a fitting of the robotic device.

As can be appreciated, the joints 1015 and 1020 may be configured so that the horizontal linkage 1002 may only move in a plane oriented parallel to a lateral axis defined by the stationary components. Accordingly, the robotic device may be adjusted laterally, e.g., after the first anchor component 1004 and the second anchor component 1006 are engaged. In fact, the horizontal linkage 1010 may afford adjustment along a third axis of movement, e.g., forward or backward relative to the plane that would contain the lateral axis defined by the stationary components and the longitudinal plane defined by the elongate holder 1002. Depending on the type of robotic device, this additional range of motion (e.g., compared to the holding device 100 (FIG. 1)) may be advantageous. In operation, the robotic device may be maneuvered to a desired position and then the joints 1015 and 1020 locked, e.g., a position of the robot mount 1026 may be selectively adjustable and lockable relative to the elongate holder 1002.

Holding devices comprising one or more patient positioning sockets that may receive a patient positioner and one or more mounts for securely mounting a robotic device are described. Accordingly, surgical device supports of the present disclosure may allow for simultaneous mounting of a robotic device and a patient positioner in close proximity to one another along the bed rail or other structure, which may improve the ability to optimally position a patient for a robotic or robot-assisted surgical procedure.

A multifunctional holding device may include an elongate holder, at least one anchor component, and at least one patient stabilization connector. The at least one anchor component and the at least one patient stabilization connector may extend laterally from the channel of the holding arm, which may translate longitudinally relative to the anchor component and patient stabilization connector. The anchor component may attach to a structure, e.g., a bed rail, to secure the holding device thereto. The patient stabilization connector may receive a portion of a patient positioner when the anchor component is attached to the support such that the patient positioner may be used to place and/or stabilize a patient in a desired position. For example, a portion of the patient positioner is received within the socket and a pad of the patient positioner may be located in the general vicinity of the patient anatomy intended for stabilization, and may require only fine or minor adjustments of the patient positioner to account for patient-specific anatomy.

In a first embodiment, a holding device for securing a surgical robotic device and a patient anatomy positioner to a support is provided, the holding device comprising a carriage, an anchor component fixed to the carriage for attaching to the support, a patient stabilization connector extending from the anchor component for attaching to the patient positioner, and an elongate holder slidably mounted on the carriage for attaching to the robotic device, wherein, when the anchor component is attached to the support, the carriage and the patient stabilization connector are immobilized. In some examples, the elongate holder is limited to longitudinal translational movement with respect to the carriage and the patient stabilization connector. In some examples, the patient stabilization connector further comprises a socket for receiving a portion of the patient positioner. In some examples, the anchor component comprises a set of lockable jaws for engaging the support. In some examples, the support is a bed rail in an operating theater. In some examples, the anchor component is affixed to a first side of the carriage. In some examples, a second anchor component is affixed to a second side of the carriage. In some examples, the elongate holder comprises a mounting plate for attaching to the robotic device and a plurality of parallel, spaced apart, rails extending from the mounting plate and engaging the carriage. In some examples, the carriage further comprises a pair of longitudinally arranged rail receptacles for engaging at least one of the plurality of rails. In some examples, the carriage further comprises a guide wheel for engaging at least one of the plurality of rails. In some examples, the plurality of rails define a space between them and the carriage is disposed in the space. In some examples, a hydraulic cylinder is also at least partially disposed in the space, wherein a first portion of the hydraulic cylinder is connected to the elongate holder and a second portion of the hydraulic cylinder is connected to the carriage. In some examples, the hydraulic cylinder holds the elongate holder and robotic device in a vertical position in the absence of a translating adjusting force. In some examples, a horizontal linkage is interposed between the elongate holder and the robotic device, the horizontal linkage comprising at least one joint.

In a second embodiment, a surgical holding device is provided, comprising a carriage, an anchor component fixed to the carriage for attaching to a support in an operating theater, a patient stabilization connector extending from the anchor component for attaching to a patient positioner, an elongate holder slidably mounted on the carriage for attaching to a horizontal linkage comprising at least one joint, wherein horizontal linkage is for attaching to a robotic device, and a hydraulic cylinder, wherein a first portion of the hydraulic cylinder is connected to the elongate holder and a second portion of the hydraulic cylinder is connected to the carriage, wherein, when the anchor component is attached to the support, the carriage and the patient stabilization connector are immobilized. In some examples, the hydraulic cylinder holds the elongate holder and robotic device in a vertical position in the absence of a translating adjusting force. In some examples, the elongate holder is limited to longitudinal translational movement with respect to the carriage and the patient stabilization connector. In some examples, a second anchor component is affixed to a side of the carriage opposite the first anchor component.

In a third embodiment, a method of connecting a surgical robotic device and a patient anatomy positioner to a single position on a support is provided, comprising mounting the robotic device to an elongate holder, mounting the patient positioner to a patient stabilization connector, providing a carriage and slidably connecting the carriage to the elongate holder and fixedly connecting the carriage to the patient stabilization connector, connecting the carriage to an anchor component fixed to the carriage, and attaching to the anchor component to the support. In some examples, the method further comprises connecting a first portion of a hydraulic cylinder to the elongate holder and a second portion of a hydraulic cylinder to the carriage.

In a fourth embodiment, a holding device is provided, comprising an elongate holder having a proximal end configured to receive a robotic device and a distal end with a longitudinal axis extending therebetween and a channel extending perpendicular to the longitudinal axis along at least a portion of a length of the elongate holder; an anchor component configured to attach to a support, the anchor component extending laterally from the channel of the elongate holder; and a patient stabilization connector extending laterally from the anchor component, the patient stabilization connector having a body configured to receive a patient positioner when the anchor component is attached to the support. In some examples, the elongate holder may translate longitudinally relative to the anchor component. In some examples, the patient stabilization connector may translate laterally relative to the anchor component. In some examples, the patient stabilization connector includes a socket to receive a portion of the patient positioner. A lateral distance between the socket and the elongate holder may be a fixed distance when the anchor component attaches to the support based on an intended surgical procedure to be performed with the robotic device.

In some examples, the device further comprises a second anchor component configured to attach to the support, wherein the anchor component extends laterally from a first side of the channel of the elongate holder and the second anchor component extends laterally from a second side of the channel. In some examples, the device further comprises a second patient stabilization connector extending laterally from the second anchor component, the second patient stabilization connector having a body configured to receive a patient positioner when the second anchor component is attached to the support. In some examples, the elongate holder further comprises a first plate extending from the proximal end to the distal end of the elongate holder, the first plate having a front, a back, a first side, and a second side, and a second plate extending parallel to the first plate, the second plate having a front, a back, a first side, and a second side, wherein the channel extends between the first plate and the second plate.

In some examples, the anchor component further comprises a carriage, wherein a portion of the elongate holder is slidably received within the carriage such that the elongate holder may translate along the longitudinal axis of the holder relative to the carriage. A first post and a second post of the elongate holder are slidably received within the carriage.

In some examples, the device further comprises a drape with an expandable section, the expandable section extending over at least a portion of the elongate holder and the anchor component.

In some examples, the support is a bedrail. In some examples, the anchor component includes an adjustable clamp.

In some examples, the device further comprises a horizontal linkage with a first end coupled to the proximal end of the elongate holder and a second end configured to receive the robotic device. The horizontal linkage may be rotatably coupled to the proximal end of the elongate holder. A position of the horizontal linkage may be selectively lockable relative to the elongate holder.

In a fifth embodiment, a surgical method comprises coupling a robotic device to a proximal end of an elongate holder of a holding device, securing the holding device to a support with an anchor that extends laterally from the elongate holder, inserting a patient positioner into a patient stabilization connector that extends laterally from the anchor, and stabilizing a portion of patient anatomy with the patient positioner during use of the robotic device. In some examples, the method further comprises translating the elongate holder along a longitudinal axis extending between the proximal end and a distal end of the elongate holder relative to the anchor and the patient positioner. In some examples, the method further comprises securing the holding device to the support with a second anchor, wherein the anchor extends laterally from a first side of the elongate holder and the second anchor extends laterally from a second of the elongate holder opposite the first side. In some examples, inserting the patient positioner into the patient stabilization connector further includes inserting a post of the patient positioner into a socket of the patient stabilization connector.

In some embodiments, the holding device may include one more extensions or beams that may receive a stabilization component from a surgical instrument. Put another way, the holding device 100 may serve as a frame to stabilize a surgical instrument, e.g., a retractor, during a surgical procedure, which may reduce the number of components that require attachment to the bed rail (or other operating room structure). For example, a fishhook or other attachment feature of a retractor may be secured to or around the extension. The extension could extend from the second anchor component, for example.

Although specific embodiments are described above, changes may be made within the spirit and scope of the concepts described. For example, while the illustrated embodiments show the patient stabilization connector extending laterally from the first anchor component, in some embodiments, the patient stabilization connector may extend laterally from the second anchor component. Alternatively, the holding device may include a second patient stabilization connector that may extend from the second anchor component while the patient stabilization connector may extend from the first anchor component.

The invention claimed is:

1. A holding device for securing a surgical robotic device and a patient anatomy positioner to a support, the holding device comprising:
   a carriage;
   an anchor component fixed to the carriage for attaching to the support;
   a patient stabilization connector extending from the anchor component for attaching to the patient positioner; and
   an elongate holder slidably mounted on the carriage for attaching to the robotic device;
   wherein, when the anchor component is attached to the support, the carriage and the patient stabilization connector are immobilized.

2. The holding device of claim 1, wherein the elongate holder is limited to longitudinal translational movement with respect to the carriage and the patient stabilization connector.

3. The holding device of claim 1, wherein the patient stabilization connector further comprises a socket for receiving a portion of the patient positioner.

4. The holding device of claim 1, wherein the anchor component comprises a set of lockable jaws for engaging the support.

5. The holding device of claim 1, wherein the support is a bed rail in an operating theater.

6. The holding device of claim 1, wherein the anchor component is affixed to a first side of the carriage.

7. The holding device of claim 6, further comprising a second anchor component affixed to a second side of the carriage.

8. The holding device of claim 1, wherein the elongate holder comprises a mounting plate for attaching to the robotic device and a plurality of parallel, spaced apart, rails extending from the mounting plate and engaging the carriage.

9. The holding device of claim 8, wherein the carriage further comprises a pair of longitudinally arranged rail receptacles for engaging at least one of the plurality of rails.

10. The holding device of claim 8, wherein the carriage further comprises a guide wheel for engaging at least one of the plurality of rails.

11. The holding device of claim 8, wherein the plurality of rails define a space between them and the carriage is disposed in the space.

12. The holding device of claim 11, wherein a hydraulic cylinder is also at least partially disposed in the space, wherein a first portion of the hydraulic cylinder is connected to the elongate holder and a second portion of the hydraulic cylinder is connected to the carriage.

13. The holding device of claim 12, wherein the hydraulic cylinder holds the elongate holder and robotic device in a vertical position in the absence of a translating adjusting force.

14. The holding device of claim 1, further comprising a horizontal linkage interposed between the elongate holder and the robotic device, the horizontal linkage comprising at least one joint.

15. A surgical holding device, comprising:
    a carriage;
    an anchor component fixed to the carriage for attaching to a support in an operating theater;
    a patient stabilization connector extending from the anchor component for attaching to a patient positioner;
    an elongate holder slidably mounted on the carriage for attaching to a horizontal linkage comprising at least one joint, wherein horizontal linkage is for attaching to a robotic device; and
    a hydraulic cylinder, wherein a first portion of the hydraulic cylinder is connected to the elongate holder and a second portion of the hydraulic cylinder is connected to the carriage;
    wherein, when the anchor component is attached to the support, the carriage and the patient stabilization connector are immobilized.

16. The holding device of claim 15, wherein the hydraulic cylinder holds the elongate holder and robotic device in a vertical position in the absence of a translating adjusting force.

17. The holding device of claim 15, wherein the elongate holder is limited to longitudinal translational movement with respect to the carriage and the patient stabilization connector.

18. The holding device of claim 15, further comprising a second anchor component affixed to a side of the carriage opposite the first anchor component.

19. A method of connecting a surgical robotic device and a patient anatomy positioner to a single position on a support, comprising:
    mounting the robotic device to an elongate holder;
    mounting the patient positioner to a patient stabilization connector;
    providing a carriage and slidably connecting the carriage to the elongate holder and fixedly connecting the carriage to the patient stabilization connector;
    connecting the carriage to an anchor component fixed to the carriage; and
    attaching to the anchor component to the support.

20. The method of claim 19, further comprising connecting a first portion of a hydraulic cylinder to the elongate holder and a second portion of a hydraulic cylinder to the carriage.

* * * * *